United States Patent [19]

Prud'Homme

[11] Patent Number: 4,684,741

[45] Date of Patent: Aug. 4, 1987

[54] SELECTIVE PRODUCTION OF DIMETHYLDICHLOROSILANE

[75] Inventor: Christian Prud'Homme, Lyons, France

[73] Assignee: Rhone-Poulenc Specialites Chimiques, Courbevoie, France

[21] Appl. No.: 832,080

[22] Filed: Feb. 24, 1986

[30] Foreign Application Priority Data

Feb. 22, 1985 [FR] France ............................ 85 02550

[51] Int. Cl.$^4$ ................................................ C07F 7/08
[52] U.S. Cl. .................................................... 556/472
[58] Field of Search ................ 556/472; 502/340, 341

[56] References Cited

U.S. PATENT DOCUMENTS 2,865,939 12/1958 Little et al. ......................... 556/472
2,877,254  3/1959 Enk et al. ............................ 556/472
4,500,724  2/1985 Ward et al. ......................... 556/472

FOREIGN PATENT DOCUMENTS 0138678 4/1985 European Pat. Off. ............ 556/472
0138679 4/1985 European Pat. Off. ............ 556/472

Primary Examiner—Paul F. Shaver
Attorney, Agent, or Firm—Burns, Doane, Swecker & Mathis

[57] ABSTRACT

Dimethyldichlorosilane is selectively and efficiently prepared by reacting methyl chloride with a solid contact mass comprising silicon and a catalytically effective amount of copper or a copper compound, said copper catalyst comprising (i) from about 10 to 1000 ppm of tin, antimony, or admixture thereof, or of a tin or antimony compound, or admixture thereof, (ii) from about 0.01 to 2% by weight of at least one of the metallic additives beryllium, calcium and magnesium, or compound thereof, and, optionally, (iii) from about 0.01 to 3% by weight of zinc or a zinc compound.

17 Claims, No Drawings

SELECTIVE PRODUCTION OF DIMETHYLDICHLOROSILANE

CROSS-REFERENCE TO RELATED APPLICATION

My copending application, Serial No. 832,078, filed concurrently herewith and assigned to the assignee hereof.

BACKGROUND OF THE INVENTION

1. Field of the Invention

The present invention relates to a process and catalyst for the direct synthesis of dimethyldichlorosilane.

2. Description of the Prior Art

The industrial process for the production of organochlorosilanes, and especially dimethyldichlorosilane (hereinafter referred to as "DMCS"), is a well-known process which is particularly described in U.S. Pat. No. 2,380,995, and in the text by Walter Noll, *Chemistry and Technology of Silicones*, pp. 26–41, published by Academic Press Inc. (1968).

According to this process, known to this art as "direct synthesis" or "Rochow synthesis", organochlorosilanes, and in particular DMCS, are produced directly by reacting methyl chloride with solid silicon in the presence of copper as a catalyst, according to the reaction:

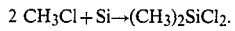

$$2\ CH_3Cl + Si \rightarrow (CH_3)_2SiCl_2.$$

In actual fact, other products are formed during the direct synthesis, especially $CH_3SiCl_3Si$ (hereinafter referred to as "MTCS") and $(CH_3)_3SiCl$ (hereinafter referred to as "TMCS").

Other by-products are also formed, such as, for example, $CH_3HSiCl_2$ and $(CH_3)_2HSiCl$, and heavy products which are polysilanes, principally disilanes.

Among all of the products obtained by direct synthesis, DMCS is the product in greatest demand. After hydrolysis and polymerization, this compound permits the preparation of oils and gums which are useful starting materials for the manufacture of silicones. Thus, DMCS is used for the preparation of polyorganosiloxane resins, as described in U.S. Pat. Nos. 2,258,218 to 2,258,222, for the preparation of oils, as described in U.S. Pat. Nos. 2,469,888 and 2,469,830, and for the preparation of polyorganosiloxane elastomers, as described in U.S. Pat. No. 2,448,756.

It is also known to this art to use copper or chemical compounds of copper as a catalyst for the direct synthesis reaction, whether employed in the form of an alloy or a mechanical mixture with silicon, optionally deposited onto an inorganic carrier or support.

Addition of various additives to the copper, in order to improve the yield of DMCS, has already been proposed to this art. These additives can be zinc or a zinc halide (U.S. Pat. No. 2,464,033), aluminum (U.S. Pat. Nos. 2,403,370 and 2,427,605), tin, manganese, nickel and silver (British Pat. No. 1,201,466), cobalt (British Pat. No. 907,161), and potassium chloride (Russian Pat. No. 307,650).

The option of using tin and antimony as an additive to the copper for controlling the reaction has already been mentioned in French Pat. No. 950,448.

French Pat. No. 1,037,183 also describes the addition of calcium, magnesium, beryllium, strontium and barium as a deoxidizing agent for the contact masses employed in the direct synthesis.

There is no doubt that the aforesaid processes employing these additives enable the direct synthesis process to be improved, but they nevertheless have at least one of the following disadvantages:

(1) The selectivity for DMCS, assessed by the average weight ratio MTCS/DMCS, and/or by the molar percentage of DMCS relative to the total amount of silanes obtained, remains inadequate;

(2) The initiation time and the initiation temperature of the reaction are too high;

(3) The mean activity of the catalyst system, also referred to as the efficiency, assessed as the weight of methylchlorosilanes (MCS) produced per hour and per kg of silicon added, and the maximum silicon conversion remain inadequate;

(4) The catalyst system is sensitive to impurities;

(5) The formation of by-products and especially of disilanes remains high.

SUMMARY OF THE INVENTION

Accordingly, a major object of the present invention is the provision of improved process/catalyst for the direct synthesis of DMCS, which improved process/catalyst at very least markedly reduces those disadvantages and drawbacks to date characterizing the state of this art.

Notably, the subject process/catalyst makes it possible to obtain:

(i) A high average selectivity for DMCS, while increasing the efficiency, that is to say, the amount of MCS produced per unit time and per unit of contact mass;

(ii) A high initial selectivity at the beginning of the reaction, which can be maintained until the final deterioration of the catalyst system;

(iii) A high maximum silicon conversion;

(iv) A low weight content of "heavy" products relative to the MCS obtained;

(v) A lower sensitivity of the catalyst system to impurities which poison the catalyst (especially lead); and (vi) A reaction temperature which is not too high.

In the description which follows, the percentages indicated are by weight, unless otherwise indicated.

Briefly, the present invention features a process for the preparation of dimethyldichlorosilane by reacting methyl chloride with a solid contact mass comprising silicon and a catalyst containing copper or a copper compound, said process being characterized in that the catalyst additionally contains from about 10 to 1,000 ppm (calculated as metallic tin and/or antimony) of at least one metal selected from among tin and antimony, or of a compound of tin and/or antimony, and from about 0.01 to 2%, preferably from 0.05 to 1.0% (calculated as the weight of metal) of a metallic additive selected from among beryllium, magnesium and calcium, or of a compound of these three metals, relative to the solid contact mass of silicon and catalyst.

DETAILED DESCRIPTION OF THE PREFERRED EMBODIMENTS OF THE INVENTION

More particularly according to the present invention, the subject catalyst is advantageously used in a weight concentration of 1 to 30%, preferably from 5 to 12%, relative to the total weight of the contact mass.

The catalyst can be added to the silicon in the form of an alloy or in the form of a mechanical mixture.

The copper compound employed can be, other than metallic copper, especially a copper halide or a copper oxide, for example CuO and $Cu_2O$, as described in U.S. Pat. No. 2,464,033.

Cupric chloride and cuprous chloride are exemplary copper halides. It has been demonstrated in accordance with the present invention, that in fact better results, especially in terms of selectivity and silicon conversion, are obtained when copper has been added in the form of cuprous or cupric chloride.

In one particular embodiment of the invention, the catalyst can also contain metallic zinc or a zinc compound, preferably zinc chloride or zinc oxide.

The zinc is advantageously present in a weight concentration of from 0.01 to 3%, preferably from 0.02 to 1% (calculated as metallic zinc) by weight relative to the total weight of the contact mass. Up to 90% by weight of the zinc, preferably up to 50% of zinc, may be replaced by another metal which catalyzes the chlorination of copper and/or which forms a eutectic or a low-melting phase with copper salts and/or beryllium, magnesium and calcium salts.

Aluminum, cadmium, manganese, nickel and silver are representative of suitable such metals.

In addition to the pure metals, compounds of these metals, such as, for example, halides, preferably chlorides and also carbonates and nitrates can be used as the metallic additive of beryllium, magnesium and calcium.

The compounds which are most especially suitable are $BeCl_2$, $MgCl_2$, $CaCl_2$, $BeCO_3$, $MgCO_3$, $CaCO_3$, $Be(NO_3)_2$ and $Mg(NO_3)_2$. These alkaline earth metals or metal compounds will hereinafter be referred to as "additives" according to the invention.

It is desirable that the particle size of the silicon be such that the diameter of at least 50 per cent by weight of the particles ranges from 10 to 500 μm.

Similarly, the catalyst is advantageously in the form of particles whose mean diameter preferably ranges from 1 to 100 μm. Under these particle size conditions of the contact mass, the direct synthesis reaction can be carried out using a contact mass in the form of a fluidized bed.

The direct synthesis process according to the invention can generally be conducted in one of the following three types of apparatus: a reactor of the stirred bed type, such as that described in U.S. Pat. No. 2,449,821, a reactor of the fluidized bed type, such as that described in U.S. Pat. No. 2,389,931, or in a rotary oven.

The catalyst can also be used deposited onto an inorganic particulate substance such as sand, ground silica, silica gel, alumina, ground refractory brick, oil-cracking catalysts, zeolites and calcined clays, as described in French Pat. No. 1,545,407.

The reaction typically takes place at a temperature of from 280° to 450° C, especially from 290° to 370° C.

The reaction may be carried out directly at the selected temperature without being initiated at a higher temperature, especially when the reaction temperature selected is on the order of 330° C or more, in a fluidized bed.

The weight concentration of the additive according to the invention, calculated as the weight of metal, advantageously ranges from about 0.01 to 2% by weight relative to the weight of the contact mass, preferably from 0.1 to 1.0% by weight. Below 0.01% the action of the additive is not really detectable, and above 2% by weight the additive can have a poisoning effect which reduces the selectivity markedly.

The weight concentration of tin and/or antimony and/or of tin and/or antimony compound (calculated as metallic tin and/or antimony) advantageously ranges from about 10 to 1,000 ppm, preferably from 30 to 250 ppm based on the contact mass.

There must be at least 10 ppm of tin and/or antimony. It has been demonstrated, in fact, in accordance with the invention, that the beneficial effects of the additive according to the invention are obtained only in the presence of tin and/or antimony. In addition, a weight concentration above 1,000 ppm would appear to have a detrimental effect on the reaction, and especially on the selectivity. Tin, which is the preferred metal, can be added in the form of bronze or in the form of a tin compound, for example tin chloride.

It has been demonstrated in accordance with the invention, that if it were intended to carry out the reaction at a temperature below 350°–360° C while retaining substantially the same advantages, then zinc or a zinc compound, preferably zinc chloride, could be added at a weight concentration of from 0.01 to 3%, preferably from 0.02 to 1%, based on the contact mass.

It has also been demonstrated in accordance with the present invention, that up to 90%, preferably up to 50% by weight of metal additive according to the invention (calculated as the weight of metal) could be replaced by an alkali metal or a compound of an alkali metal selected from among lithium, sodium, potassium, rubidium and cesium.

Very high selectivities can be obtained by using a catalyst according to the invention when the reaction is carried out in a stirred bed at a temperature of 330°–350° C.

Thus, it is possible to obtain a mean MTCS/DMCS weight ratio on the order of or below 0.07 and capable of reaching 0.05, and a mean molar percentage of DMCS based on the total silanes obtained on the order of or above 85% and capable of reaching 92%, a maximum silicon conversion on the order of or above 50% and capable of reaching approximately 85%, and a mean activity on the order of or above 125 g of MCS/h/kg of Si, and capable of reaching 180 g MCS/h/kg of Si, and higher.

A selectivity on the order of or above 90% appears to be especially surprising, compared to the selectivities obtained by using catalyst masses of the same type but not including an additive according to the invention, as is apparent from the examples in French Pat. No. 1,545,407.

Furthermore, when a contact mass according to the invention, but not containing tin and/or antimony is employed, a contact mass which is relatively inactive and hence industrially unacceptable is obtained, as shown by the comparative example below.

The percentage of heavy materials obtained, relative to the MCS obtained, can be on the order of 2% and is generally below about 4%.

These results can be further improved if the reaction temperature is increased. Similar results are obtained when the reaction is carried out in a fluidized bed.

When the reaction is carried out in a stirred bed at a temperature below 340° C., it is desirable to initiate the reaction for a few tens of minutes at a temperature above 340° C. This initiation is unnecessary when the operation is carried out in a stirred bed at a temperature above 340° C., or when a copper chloride such as CuCl and CuCl$_2$ is employed.

In order to further illustrate the present invention and the advantages thereof, the following specific examples are given, it being understood that same are intended only as illustrative and in nowise limitative.

Unless otherwise indicated the reactor used in the examples which follow was a cylindrical pilot reactor having an internal diameter of 60 mm and was 250 mm high, equipped with a sintered glass gas distributor at its base. Silicon and the catalyst were charged in the form of a powder in which at least 50% of the particles had a mean size of from 60 to 200 µm.

The reaction was carried out in a stirred bed and the reactor was equipped with an external heating element.

EXAMPLE

Catalyst system: CuCl/CaCl$_2$/ZnCl$_2$/Sn at 330° C.

A cylindrical vertical glass reactor (diameter: 60 mm) equipped with a metal stirrer and a sintered glass gas distributor, was charged with a powder consisting of: 210 g of silicon, 16.4 g of cuprous chloride, 1.244 g of calcium chloride, 1.53 g of zinc chloride and 2.0 g of bronze containing 2% of tin. The reactor was heated gradually up to 200° C. under a stream of nitrogen. Then, while the reactor temperature continued to be increased, the nitrogen was turned off and the addition of methyl chloride was begun at a rate of 16 l/hr.

The reactor temperature was then set at 345° C. and maintained at this value for approximately one hour before being reduced to 330° C.

After 3.4 hours of operation at 330° C., the methyl chloride flow rate was increased to 27 l/hr.

This heating at 330° C. and stirring was maintained until the reaction stopped completely and spontaneously.

This test produced chlorosilanes for 15.5 hours at an efficiency equal to 165 g per hour and per kg of silicon charged into the reactor.

The mixture produced was characterized by a mean MTCS/DMCS weight ratio of 0.087, the proportion of heavy materials being 2.7% by weight.

The following mean molar selectivities were determined by gas phase chromatography:

Me$_2$SiCl$_2$: 86.7%
MeSiCl$_3$: 6.53%
Me$_3$SiCl 4.53%
Maximum silicon conversion: 55%.

COMPARATIVE EXAMPLE

Catalyst system: CuCl/CaCl$_2$/ZnCl$_2$ at 330° C.

A vertical cylindrical glass reactor (diameter: 60 mm) equipped with a metal stirrer and a sintered glass gas distributor was charged with a powder consisting of 210 g of silicon, 16.4 g of cuprous chloride, 1.244 g of calcium chloride, and 1.53 g of zinc chloride. The reactor was heated gradually up to 200° C. under a nitrogen stream. Then, while the reactor temperature continued to be increased, the nitrogen was turned off and the addition of methyl chloride was begun at a flow rate of 16 l/hr.

The reactor temperature was then set at 345° C. and maintained at this value for approximately one hour before being reduced to 330° C.

Heating at 330° C. and stirring were maintained until the reaction had stopped completely and spontaneously.

This test produced chlorosilanes for only 5 hours, at an efficiency equal to 35 g per hour and per kg of silicon charged into the reactor.

The mixture produced was characterized by a mean MTCS/DMCS weight ratio of 0.21, the proportion of heavy materials being 1.56% by weight.

The following mean molar selectivities were determined by gas phase chromatography:

Me$_2$SiCl$_2$: 69 1%
MeSiCl$_3$: 12.6%
Me$_3$SiCl: 10.4%
Maximum silicon conversion: 8.3%.

While this invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of dimethyldichlorosilane, which comprises reacting methyl chloride with a solid contact mass comprising silicon and a catalytically effective amount of copper or a copper compound, said cooper catalyst comprising (i) from about 10 to 1,000 ppm of tin, antimony, or admixture thereof, or of a tin or antimony compound, or admixture thereof, (ii) from about 0.05 to 2% by weight of at least one of the metallic additives beryllium, calcium and magnesium, or compound thereof, and (iii) from about 0.01 to 3% by weight of zinc or a zinc compound.

2. The process as defined by claim 1, said concentration of tin and/or antimony ranging from about 30 to 250 ppm.

3. The process as defined by claim 1, up to 90% by weight of said zinc component (iii) being replaced by (iv) a copper chlorination metal catalyst and/or metal forming a eutectic or low-melting phase with copper salts and/or beryllium, magnesium and calcium salts.

4. The process as defined by claim 3, said metal (iv) comprising aluminum, cadmium, manganese, nickel, or silver.

5. The process as defined by claim 1, said copper catalyst comprising from about 0.02 to 1% by weight of zinc or a zinc compound.

6. The process as defined by claim 1, said copper catalyst comprising from about 1 to 30% by weight of said solid contact mass.

7. The process as defined by claim 6, said copper catalyst comprising metallic copper, cuprous chloride, or cupric chloride.

8. The process as defined by claim 1, said copper catalyst comprising metallic zinc, zinc chloride, or zinc oxide.

9. The process as defined by claim 1, said metallic additive (ii) comprising BeCl$_2$, MgCl$_2$, CaCl$_2$, BeCO$_3$, MgCO$_3$, CaCO$_3$, Be(NO$_3$)$_2$ or Mg(NO$_3$)$_2$.

10. The process as defined by claim 1, said solid contact mass comprising particulate silicon.

11. The process as defined by claim 10, the diameter of at least 50% by weight of said silicon particles ranging from about 10 to 500 µm.

12. The process as defined by claim 11, said solid contact mass comprising particulate catalyst.

13. The process as defined by claim 12, the mean diameter of said catalyst particles ranging from 1 to 100 µm.

14. The process as defined by claim 1, wherein said copper catalyst is deposited onto an inorganic particulate substrate therefor.

15. The process as defined by claim 1, carried out in a fluidized bed.

16. The process as defined by claim 1, carried out in a stirred bed.

17. The process as defined by claim 1, carried out in a rotary oven.

* * * * *